(12) United States Patent
Ogrodnik et al.

(10) Patent No.: US 10,226,214 B2
(45) Date of Patent: Mar. 12, 2019

(54) BONE FIXATION SYSTEM AND ASSOCIATED METHOD

(71) Applicants: Peter Jan Ogrodnik, Shropshire (GB); Peter Brian MacFarlane Thomas, Shropshire (GB)

(72) Inventors: Peter Jan Ogrodnik, Shropshire (GB); Peter Brian MacFarlane Thomas, Shropshire (GB)

(*) Notice: Subject to any disclaimer, the term of this patent is extended or adjusted under 35 U.S.C. 154(b) by 111 days.

(21) Appl. No.: 14/915,629

(22) PCT Filed: Sep. 12, 2014

(86) PCT No.: PCT/GB2014/052799
§ 371 (c)(1),
(2) Date: Feb. 29, 2016

(87) PCT Pub. No.: WO2015/036784
PCT Pub. Date: Mar. 19, 2015

(65) Prior Publication Data
US 2016/0213319 A1 Jul. 28, 2016

(30) Foreign Application Priority Data

Sep. 12, 2013 (GB) .................................. 1316263.1
Jul. 29, 2014 (GB) .................................. 1413401.9

(51) Int. Cl.
*A61B 5/00* (2006.01)
*A61B 5/01* (2006.01)
(Continued)

(52) U.S. Cl.
CPC .............. *A61B 5/6812* (2013.01); *A61B 5/01* (2013.01); *A61B 5/1036* (2013.01); *A61B 5/11* (2013.01);
(Continued)

(58) Field of Classification Search
CPC . A61B 5/6812; A61B 5/7246; A61B 5/14546; A61B 5/1036; A61B 5/7282;
(Continued)

(56) References Cited

U.S. PATENT DOCUMENTS 5,738,684 A 4/1998 Thomas
6,034,296 A 3/2000 Elvin
(Continued)

FOREIGN PATENT DOCUMENTS

EP 0740927 12/2000
EP 1905388 1/2012
(Continued)

OTHER PUBLICATIONS

International Preliminary Report on Patentability dated Mar. 15, 2016 for PCT/GB2014/052779 in the name of IN. MEDICA D.O.O.

*Primary Examiner* — Rex R Holmes
(74) *Attorney, Agent, or Firm* — Richard Batt

(57) ABSTRACT

A method of monitoring a bone fracture in an individual. The method comprises the steps of: measuring a first parameter indicative of the load on said bone fracture; measuring a second parameter indicative of the activity level of said individual; obtaining a plurality of values for said first and second parameters; correlating said values to determine a measure of bone fracture condition; monitoring a change in said correlation over time; and determining a measure of the change in bone fracture condition over time. A bone fixation system implements this method of monitoring a bone fracture in an individual. The method and system provide a more accurate and reliable measure of bone fracture condition and of the progression of healing of the bone fracture.

4 Claims, 14 Drawing Sheets

(51) Int. Cl.
*A61B 5/11* (2006.01)
*A61B 5/103* (2006.01)
*A61B 5/145* (2006.01)
*A61M 5/142* (2006.01)
*A61B 17/60* (2006.01)
*A61B 17/68* (2006.01)
*A61B 17/70* (2006.01)
*A61B 17/72* (2006.01)
*A61B 17/80* (2006.01)

(52) U.S. Cl.
CPC ........... *A61B 5/1118* (2013.01); *A61B 5/1121* (2013.01); *A61B 5/14542* (2013.01); *A61B 5/14546* (2013.01); *A61B 5/4504* (2013.01); *A61B 5/486* (2013.01); *A61B 5/4836* (2013.01); *A61B 5/6846* (2013.01); *A61B 5/6847* (2013.01); *A61B 5/6878* (2013.01); *A61B 5/7246* (2013.01); *A61B 5/7282* (2013.01); *A61B 5/00* (2013.01); *A61B 5/0022* (2013.01); *A61B 5/0024* (2013.01); *A61B 5/1126* (2013.01); *A61B 5/4848* (2013.01); *A61B 17/60* (2013.01); *A61B 17/68* (2013.01); *A61B 17/70* (2013.01); *A61B 17/72* (2013.01); *A61B 17/80* (2013.01); *A61B 2562/0219* (2013.01); *A61B 2562/0247* (2013.01); *A61B 2562/0252* (2013.01); *A61B 2562/0261* (2013.01); *A61B 2562/0266* (2013.01); *A61M 5/142* (2013.01); *A61M 2210/02* (2013.01)

(58) Field of Classification Search
CPC ... A61B 5/4836; A61B 5/486; A61B 5/14542; A61B 5/1118; A61B 5/6846; A61B 5/6847; A61B 5/6878; A61B 5/01; A61B 5/11
See application file for complete search history.

(56) References Cited

U.S. PATENT DOCUMENTS

| | | |
|---|---|---|
| 2012/0065548 A1 | 3/2012 | Morgan |
| 2012/0071735 A1 | 3/2012 | Caylor, III |
| 2012/0277746 A1* | 11/2012 | Morgan ............... A61B 5/0031 606/62 |
| 2012/0163683 A1 | 12/2012 | La Rue |
| 2013/0044174 A1 | 7/2013 | Stein |
| 2013/0090732 A1 | 9/2013 | Muller |
| 2013/0190654 A1 | 12/2013 | Shimizu |

FOREIGN PATENT DOCUMENTS

| | | |
|---|---|---|
| WO | 2005/120203 | 12/2005 |
| WO | 2007/025191 | 3/2007 |
| WO | 2011/044220 | 4/2011 |

* cited by examiner

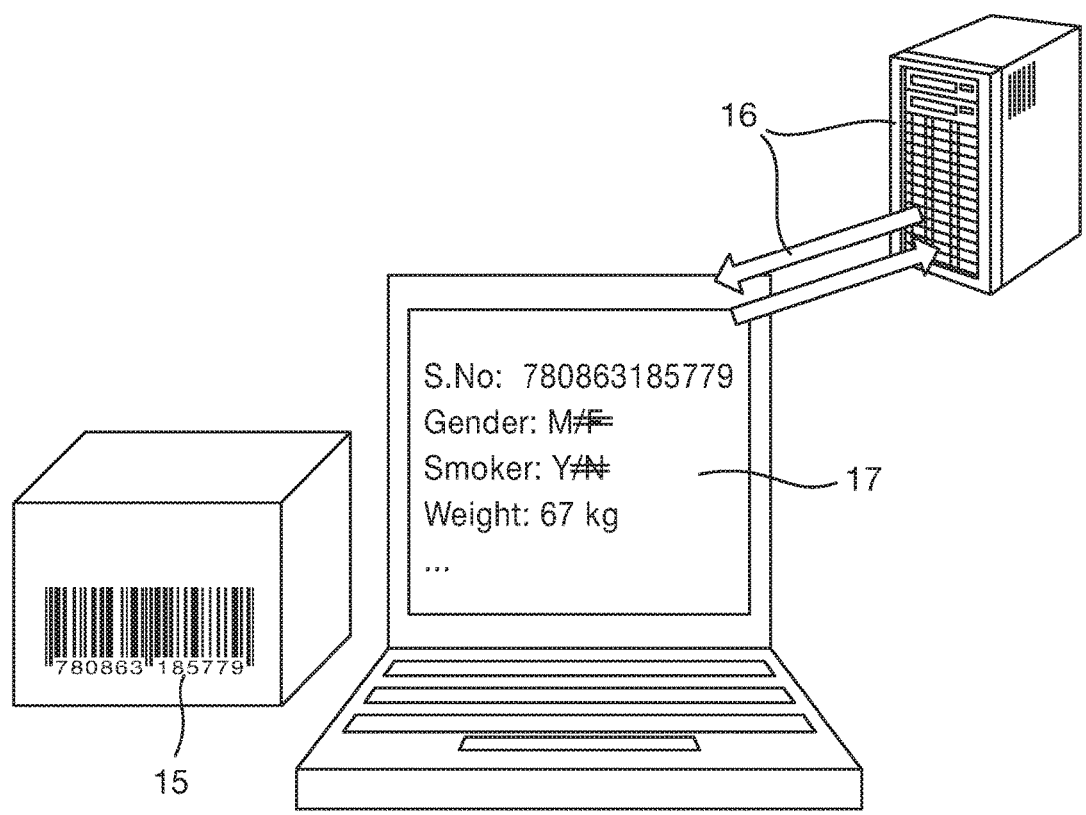

BONE FIXATION SYSTEM AND ASSOCIATED METHOD

The present invention relates to a method of monitoring a bone fracture in an individual and to a bone fixation system which can perform said method.

All vertebrates with a solid skeletal frame can suffer a fracture of one or more bones. The natural healing process of long bones creates callus as a product of inter-fragmentary movement; the callus mass builds until the movement comes to rest. At this point the bone is healed. However, there are complications and congenital issues that could delay this process. When treating a human with, say, a fractured tibia the surgeon has a variety of choices of treatment regime. Stable fractures (those that do not shorten under axial loading) are treated in plaster-of-paris casts; unstable fractures are treated surgically using external fixation or internal fixation. But they are all bound by the same questions: is the fracture healing as it should? Is the fracture heading towards a non-union? Is the fracture healed and is it time to remove the fixation? At present, all of these questions are answered by examining patients at regular clinics.

Typically a patient suffering say a tibial fracture, would be required to visit about 4-6 clinics over a period of several months. However this is a cumbersome approach; it involves transportation to and from hospitals, and dictates the use of resources to staff clinics. As an example, for the tibia, the surgeon would start to assess healing after about 7 weeks. This involves examination of x-ray images and physical manipulation of the fracture. Of course, in between clinics the patient is self diagnosing by observing for infections etc. The clinic therefore is a synthesis of a variety of data to decide whether the fracture healing is progressing 'normally'. In the early stages the decision concerns how the healing is progressing and whether there are any complications (such as mal-union, infection or non-union ensuing). In the latter stages the decision concerns whether the fracture is healed or not. In both cases early intervention of any complication is of paramount importance. In the case of early detection of a complication the benefits are self evident. In the case of fracture healing detection a patient's fracture could be considered healed one day after their last clinic. Being missed by one day, the fixation could be in place for a number of weeks longer than it needs to be; or the patient cannot return to normal activity for longer than necessary. Any improvement in the situations described above would realise cost benefits for the healthcare provider and personal benefits for the patient.

EP-A-0740927 and U.S. Pat. No. 5,738,684, previously filed by the inventors of the present invention, provide basis for a fixation system in concept concerned with obtaining continuous information about use of a bone fixation system on a patient, and particularly concerned with determining the degree of relative movement between fractured bones.

Other documents have not taken the concept much further and have not extended the technology, but have demonstrated the need for an improved system. US-A-2012277746 presents an instrumented IM nail, and US-A-2012065548 presents an instrumented plate, and US-A-2012163683 is similarly presented for an implant, but these do not improve on the technology of EP-A-0740927 and U.S. Pat. No. 5,738,684. WO-A-2013044174 presents a telemetric implant for condition monitoring of said implant, and concentrates on the design of the implant itself. EP-A-1905388 and US-A-2012071735 disclose systems concerned with tele-health associated with implants, the former is not an automatic system and relies on a call centre, the latter is concerned with data within a hospital environment only. However, none of theses documents disclose the technology required for successful implementation of an independent data-logging and monitoring system i.e. an intelligent fixation system.

The present invention is set out in the appended claims. Embodiments of the present invention are generally concerned with correlating parameters associated with a bone fracture and the individual, as it has been found that this provides a more accurate and reliable measure of bone fracture condition. Additionally, embodiments of the present invention may monitor a change in that correlation over time, since it has been found that this provides a more accurate and reliable measure of the progression of healing of the bone fracture.

Embodiments of the present invention proposes a system that incorporates sensors, data logging, transmission and analysis of data, and personalised (secure) data presentation that, in the first instance, can be used to monitor the progression of healing of a fracture but which can be used as a platform for the monitoring of a variety of clinical outcomes away from the hospital/clinical environment.

According to the present invention there is provided a method of monitoring a bone fracture in an individual, the method comprising the steps of:

measuring a first parameter indicative of the load on said bone fracture;

measuring a second parameter indicative of the activity level of said individual;

obtaining a plurality of values for said first and second parameters;

correlating said values to determine a measure of bone fracture condition;

monitoring a change in said correlation over time; and determining a measure of the change in bone fracture condition over time.

This method may provide a more accurate and reliable measure of bone fracture condition than prior art methods and a more accurate and reliable measure of the progression of healing of the bone fracture. It may allow for self monitoring of a patient with a bone fracture. It may allow for checks linked to the healing of the bone fracture to be carried out remotely and regularly to ensure that the patient can enhance their rate of recovery and capture any complications quickly, or even as they occur. If a patient is alerted to complications quickly, they are more likely to be able to correct them quickly, minimising the delay to recovery. The method may allow for complications to be resolved remotely so the patient may not need to wait until they can get an appointment at a clinic to have them resolved. As such, the method may reduce the number of clinics a patient needs to attend, reducing the burden on the healthcare provider and the potential inconvenience to the patient in getting to the clinic.

The first parameter may be, but is not limited to: inter-fragmentary movement; deformation; acceleration; pressure; strain; and any combination(s) thereof. Such parameters may be able to give an indication of whether bones at the bone fracture site are moving an appropriate amount. The first parameter may provide a measure of deformation at the fracture site. The first parameter may be measured continuously. This would allow for constant monitoring of the fracture so would be effective in identifying any issues that may arise quickly. Alternatively, the first parameter may be measured intermittently.

The second parameter may be, but is not limited to: limb (e.g. hip) movement; acceleration; orientation; and any combination(s) thereof. Such parameters may be able to provide information on whether the patient is, for example, walking quickly, sitting down, very active, not active enough. The second parameter may be measured continuously. Alternatively, the second parameter may be measured intermittently.

The method may further comprise the steps of:
measuring a third parameter associated with said bone fracture;
obtaining a plurality of values for said third parameter;
correlating said values to determine a measure of bone fracture condition;
monitoring a change in said correlation over time; and
determining a measure of the change in bone fracture condition over time.

Measuring a third parameter may allow for an even more accurate and reliable measure of bone fracture condition and/or an even more accurate and reliable measure of the progression of healing of the bone fracture.

The third parameter may be, but is not limited to: temperature; lactic acid level; limb (e.g. hip) movement; acceleration; orientation; strain; pressure; oxygen level; tension; and any combination(s) thereof. Such parameters may provide an indication of whether a bone fracture is healing correctly. Such parameters may be able to provide an indication of whether the fracture site has become infected. The third parameter may be any other parameter associated with the patient and/or their fracture. The third parameter may be measured continuously. Alternatively, the third parameter may be measured intermittently. There may be multiple further parameters and this is not intended to be limiting.

On measuring at least one of said parameters to obtain a value, the method may further comprise the step of: comparing said at least one measured parameter value to at least one threshold value. An event may be recorded when this at least one threshold is exceeded. This may generate a useful parameter related to movement of the patient. For instance, the number of events measured per day may be used to indicate patient activity levels and/or mobility at the fracture site. This can give important indications of whether a patient is moving a correct amount to encourage healing and/or whether a fixator applied at the fracture site may be applied too tightly or not tightly enough such that it is hindering the healing process. An indicating means may be activated when said threshold is exceeded. This may be helpful in identifying problems which may arise with the fracture. For instance, if the temperature at the fracture site exceeded a threshold, this may be indicative of an infection. The indicating means may alert the patient to attend a clinic as soon as possible. The indicating means may be, but is not limited to, a loudspeaker, display, LED, an alarm or any other suitable indicating means.

Correlating said values may involve plotting a graph. This may be a useful way of identifying trends.

Determining a measure of the change in bone fracture condition over time may further comprise the step of: comparing said correlated data with pre-determined data typical of healing bone fractures. This may make it easy to identify the progression of healing and/or if there are any associated problems. The pre-determined data may comprise any, some or all of average, upper and lower boundaries for values of said correlated data typical of healing bone fractures. This may be particularly useful when the correlated data is plotted on a graph and the boundaries may be plotted as data curves on the graph. This may increase positivity and morale in a patient if they know that their fracture is healing well. It may also motivate the patient to correct their behaviour if this is having a negative effect on the healing. For instance, if the graph shows that the patient is not being active enough, it may motivate the patient to be more active.

The method may further comprise the step of: using a database as a basis for generating the pre-determined data, wherein said database is updated at regular intervals. The regular intervals may be pre-determined and/or may be controlled by activation means. The activation means may be a switch which may be controlled by the patient and/or by a physician/clinician caring for the patient. The database may be updated via wireless connections. The wireless connection may be the Internet. All data generated by such methods may be sent to a main server which uploads data to the database. The database may always contain the most up-to-date data, particularly useful when determining average, upper and lower boundary values of the correlated data, typical of healing bone fractures.

The method may further comprise the step of: providing an output based on at least one of said determinations. The output may be in the form of: text; graphic; sound; tactility; light; as any combination(s) thereof or any other suitable form. Particular forms of output may be more useful depending on the parameters measured and/or the patient/physician/clinician may have a preference as to how they would like to receive/view information. Providing an output may involve providing feedback on any, some or all of: whether the bone fracture is healing; the progression of healing of the bone fracture; predicting the endpoint of the healing process; whether a problem has developed with the bone fracture; whether the patient is not active enough or is too active. Predicting the endpoint of the healing process may comprise the steps of: extrapolating said correlated data to a point representing a healed bone fracture based on said pre-determined data; and calculating a time period over which the fracture can be expected to reach said point. The time period may be calculated directly as a result of the extrapolation, and/or may be calculated based on any, some or all of: known rates of healing; how far along the patient is into the healing process based on measured parameters or otherwise; how the healing is progressing based on correlated or monitored data or otherwise; when the fracture occurred; and/or how long a bone fixator may have been applied for.

The method may further comprise the steps of: detecting whether there is a problem associated with a bone fixator applied to the bone fracture based on at least one of said determinations; and, if a problem is detected, identifying said problem and sending feedback commands to an actuation means for manipulating said bone fixator based on the identified problem. The bone fixator may be internal or external. The steps of identifying said problem, sending feedback commands and manipulating said bone fixator, may be automatically controlled. Alternatively, or additionally, actuation may be manually controlled. This may help speed up the rate of recovery since the patient may not need to attend a clinic in order to correct a problem.

The present invention provides a bone fixation system operable to implement the method as described above.

The present invention provides a bone fixation system comprising:
a bone fixator for application to a bone fracture site;
a first sensor for measuring a first parameter indicative of load on said bone fracture and generating associated first parameter data;

a second sensor for measuring a second parameter indicative of the activity level of said individual and generating associated second parameter data;

a processing means for correlating said first and second parameter data to determine a measure of bone fracture condition, and for determining a change in said correlation over time to determine a measure of the change in bone fracture condition over time.

The bone fixation system provides the same and/or similar advantages as those of the method of the present invention.

The first sensor may be, but is not limited to: an accelerometer; a strain gauge; a pressure gauge; a capacitive sensor; or any combination(s) thereof. The first sensor may take measurements continuously. The first sensor may take measurements intermittently.

The second sensor may be, but is not limited to: a pedometer; an accelerometer; a gyroscope; a GPS sensor; or any combination(s) thereof. The second sensor may take measurements continuously. The second sensor may take measurements intermittently.

The bone fixation system may further comprise a third sensor. The third sensor may be, but is not limited to: an accelerometer; a strain gauge; a pressure gauge; a capacitive sensor; a pedometer; a gyroscope; a GPS sensor; a thermometer; or any combination(s) thereof. The third sensor may take measurements continuously. The third sensor may take measurements intermittently.

The processing means may compare any, some or all of said measured parameters to at least one threshold and record an event when this at least one threshold is exceeded. Additionally or alternatively, the processing means may compare any, some or all of said measured parameters to at least one level of activity and record an event when this activity level is met. The bone fixation system may further comprise an indicating means which may be operable to automatically activate when the at least one threshold is exceeded and/or the at least one level of activity is met.

The processing means may be able to identify a problem associated with the bone fracture or bone fixator applied thereto.

The bone fixation system may comprise an actuation means, such that the processing means may be able to send data commands to said actuation means based on an identified problem, and said actuation means may be operable to move at least a part of said bone fixator in response to said data commands. The bone fixation system may further comprise injecting, and/or stimulating means, operable to inject medication and/or antibiotics, and/or stimulate a body part, in response to said data commands. The stimulation may be electrical, thermal or any other physical stimulation. The processing means may be able to check that that the data commands and response thereto have corrected any problem with the bone fracture and/or the bone fixator.

The bone fixation system may further comprise an output means for providing an output based on at least one of said determinations. The output means may be, but is not limited to, a display, a speaker, or a combination thereof.

The bone fixation system may comprise a data storage means. The system may comprise a communication means and a device, wherein said communication means communicates data with said device. The communication means may be operable to communicate said data with said device synchronously. The communication means may be operable to communicate said data with said device asynchronously. The data may be communicated with said device via a wireless connection. The data may be communicated via the internet. In the situation where the communication means cannot send data to the device as soon as it is measured, for lack of an internet connection or otherwise, one or more of these features would allow for later transmission of the data to the device.

The device may be attached to the bone fixator. The device may be at a remote location. The device may be a server. The server may have the ability to assimilate and collate patient data into normal data for the population.

The bone fixator may have a unique identification number associated with it and any data communicated from said communication means may be communicated with this number. This may ensure that any data communicated from the bone fixation system could be traced to that particular system/fixator and/or patient. This may be helpful for a clinician observing the data remotely and/or may allow a system to automatically recognise the system/fixator and/or user for which data would need to be stored and/or where to send any data back to. Data communicated from the communication means may additionally, or alternatively, be sent anonymously.

The communication means and/or the device may be operable to push and pull data from one another. This is particularly useful when someone wants to analyse the progress of a patient since they could request data to be transmitted from the bone fixation system at will in a pull mode, but also if the bone fixation system detects the onset of a complication then the system could contact someone, such as a clinician, in a push mode.

The device may be operable to collect said data from said communication means at regular intervals; analyse said data; store said data; and communicate the results of said analysis back to said communication means for outputting on an output device. The data may be stored anonymously for use in creating graphs to display typical recovery information. The patient to whom the data corresponds may alternatively be stored with the data, which may be particularly useful if the information is to be sent onto a clinician for example.

The communication means and/or the device may be operable to receive data or other information so as to update at least one algorithm associated with the device, the algorithm being used to determine the measure of the change in bone fracture condition over time, the progress of the healing of the bone fracture, etc. The communication means and/or the device may be operable such that the algorithm is updated remotely, for example by a physician or clinician, for example over the Internet or via other communication such as short or long range wireless communication. The communication means and/or the device may be operable with more than one algorithm (any one or more of which may be updateable as discussed above), the different algorithms being configured to provide the same and/or different results, end points or targets. This may be particularly advantageous for redundancy purposes and/or for error checking between the algorithms and/or for comparative methodologies, etc.

The device may further comprise a storage means for storing data and a programmable processing means operable to use said stored data to plot graphs related thereto. The programmable processing means may be operable to calculate a data point on one of said graphs, from data communicated to said device from said communication means, and plot this point on said graph. This may be useful in comparing an individual patient's data to grouped data based on results considered normal for a healing fracture. The programmable processing means may be operable to automatically update said storage means on communication of data to said device. This would mean the storage means was regularly updated and would provide an up-to-date database for plotting graphs therefrom.

Additionally, or alternatively, the processing means may be operable to perform any of the functions as described for any part of the device. Additionally, or alternatively, parts of the device may be operable to perform any of the functions as described for the processing means. Where the processing means and device perform the same operations, one may be used as a back up system.

It should be understood that the bone fixation system of the present invention may incorporate any, some or all of the features of the method of the present invention as is desired or appropriate. Any steps in the method of the present invention may be performed by the relevant features of the bone fixation system, and the above described inventive method encompasses and may be implemented with any embodiments or any features described in connection with the previously discussed inventive bone fixation system, as long as those embodiments or features are compatible with the method.

Advantages of embodiments of the present invention may include:
- Reducing the number of clinics a patient needs to attend (indeed it is possible to eliminate the need for any clinics) this reduces burden on the healthcare provider and on the patient themselves;
- Monitoring progression of healing with a view to the capture of complications as quickly as possible;
- Transmitting and presenting data such that the surgeon/clinician is able to compare progression against 'norms';
- Transmitting and presenting data such that the patient can see their progress against norms and thus have the opportunity to be motivated.

Embodiments of the present invention will now be described, by way of example only, with reference to the accompanying drawings, of which:

FIG. 7 shows an example registration of a data-logging system;

Figure 1:
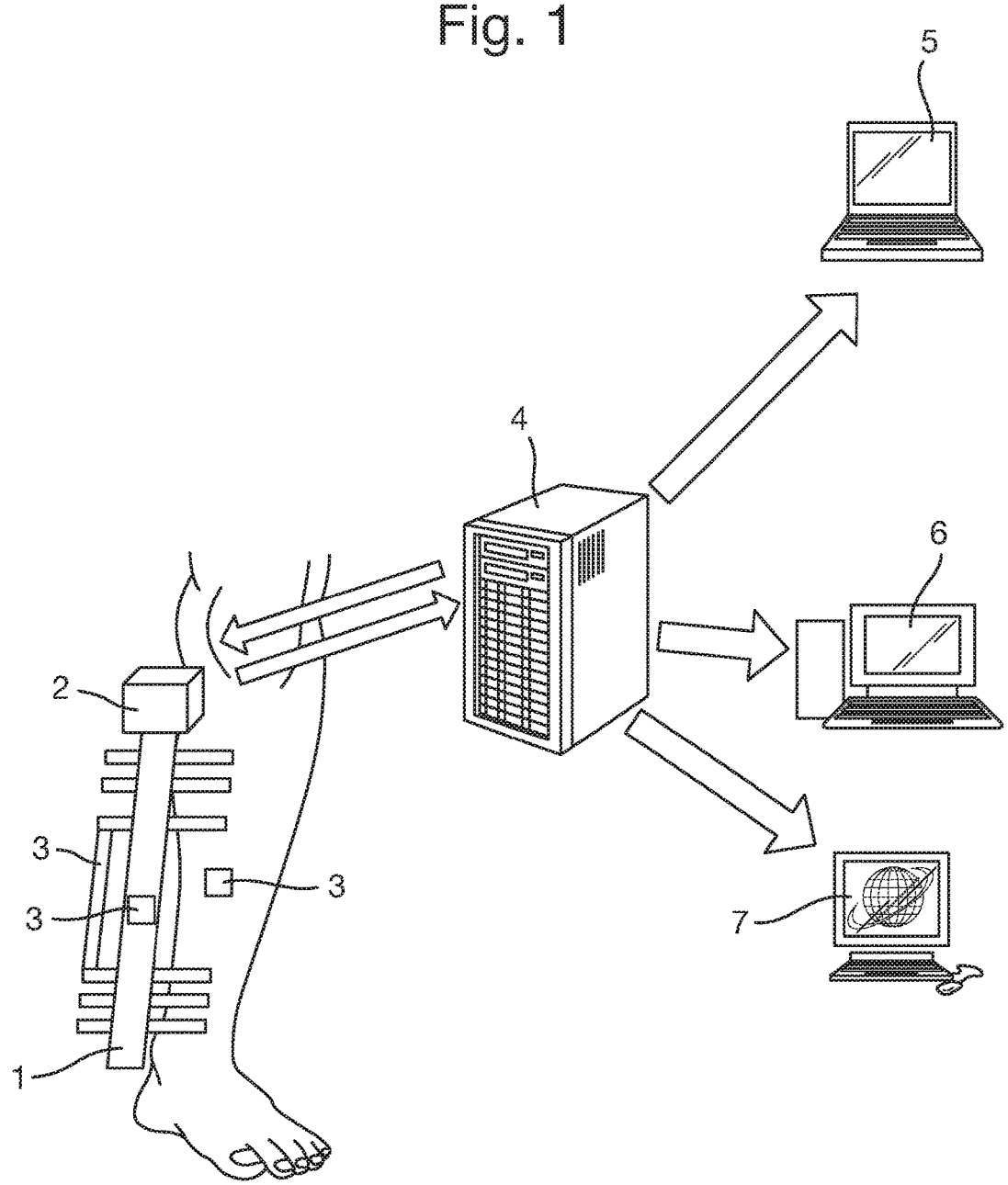
FIG. 1 shows an embodiment of a bone fixation system operable to implement the method of the present invention.

FIG. 1 is a typical embodiment of the bone fixation system. The bone fixation system is operable to implement the method of the present invention. A bone fixator (1) (for the sake of clarity this is illustrated as an external fixator but could be any fixation system such as an intramedullary nail, a plate or any other applicable fixation method) is used to fix a fracture. Attached to the fixation is a data-logging system (2). This has the ability to log data in a variety of forms, store this data and transmit this data. The data logging system could be integral to the fixation, or it could be a stand alone item. In addition to item (2) a variety of one or more sensors will be required to measure parameters of the patient, which are of importance (3). These parameters may be, but are not limited to, interfragmentary movement, pedometer data, fracture site temperature, lactic acid levels, measured strain, compartmental pressure, elevation and/or orientation and/or attitude of the fracture and/or of the patient, e.g. a limb of the patient. The sensors themselves could be wired directly to the data-logging unit (2) or could be connected wirelessly. The data-logging unit (2) would be required to collect the data from the sensors (3), and this could be in any form for example time-domain, frequency domain or tabular, and then store this locally until it is required. One method of data analysis would be to upload the data to a main server (4), or host computer (not shown). The uploading could be conducted using wired technology, wireless technology (such as Zigbee or Bluetooth), or using internet (or cloud) technology (for example 3G, 4G or WiFi). It is anticipated, however, that the greatest strength of the invention will be the use of internet based communication to a main server (4). The uploading could be synchronous or asynchronous.

In another embodiment, a processing means (not shown) connected to the bone fixator (1) and data-logging unit (2) could perform data-analysis. The raw logged data and/or processed data could then be sent to the main server (4), or host computer (not shown), for storage and/or to provide a back-up analysis of the logged data.

Another embodiment is a complete, stand alone data-logging system with all diagnostics pre-programmed on-board.

The main server (4) has a number of main tasks. The first task will be to collect the data from patients on a regular basis. This could be in either push or pull modes. For example, the data-logging system could detect an open Wi-Fi zone and then use this internet service to upload data to the server (push); alternatively the server could 'dial' the data-logging unit and then enforce uploading of data (pull). The server's $2^{nd}$ task will be to analyse and store the data that has been uploaded. This data could be numerical, or it could be graphical (some examples are given later); equally it could be a diagnostic result. However all data may need to be stored anonymously. To this end the third task of the server will be registration of the data-logging system such that only the patient and their healthcare practitioner have access to the data (described later). The fourth task of the server will be to communicate the data to the patient (5), the healthcare provider (6) and the healthcare community (7); the preferred methodology is described more fully later. It is suggested that this communication is once again push and pull. In the context of data interrogation 5,6 and 7 would interrogate their data at will in a pull mode; however if the system detected the onset of a complication then the system would contact the healthcare provider in push mode.

Figure 2:
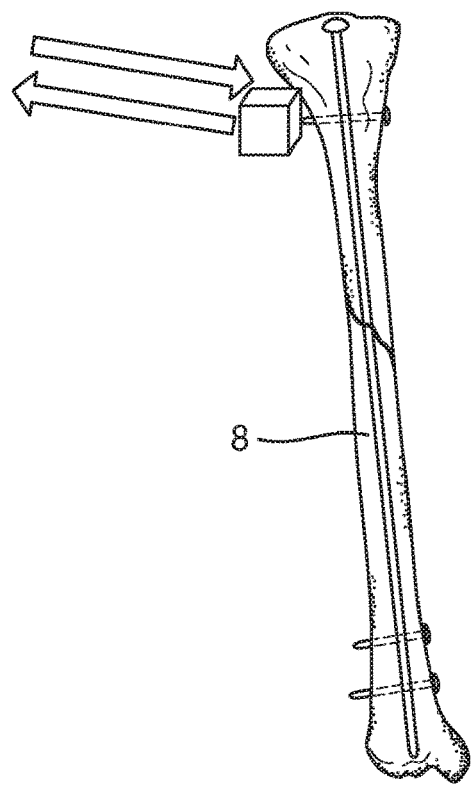
FIGS. 2-4 show embodiments of a bone fixation system for intramedullary nails, plates and plaster-of-paris casts.
Figure 3:
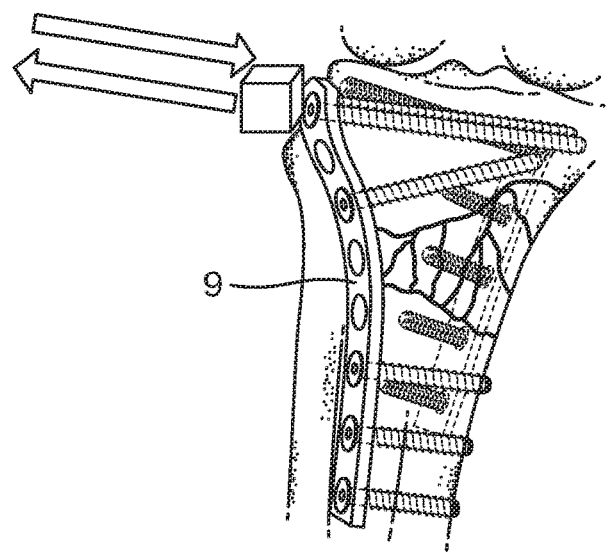
Figure 4:
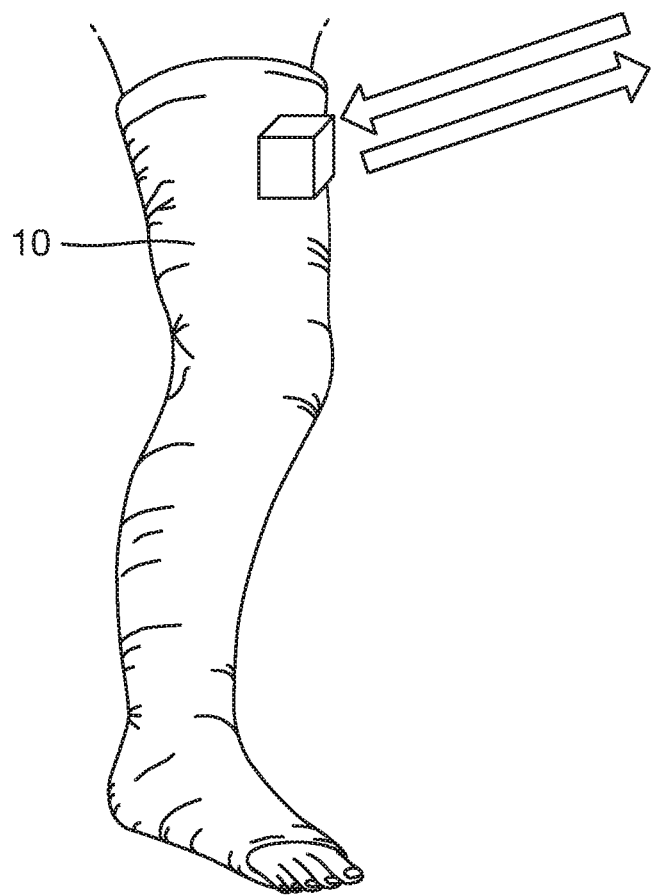

FIGS. 2, 3 and 4 illustrate further embodiments for the system illustrated in FIG. 1. FIG. 2 is an intramedullary nail (8); FIG. 3 is a plate (9); and FIG. 4 a plaster-of-paris (or other appropriate material) cast (10).

Figure 5:
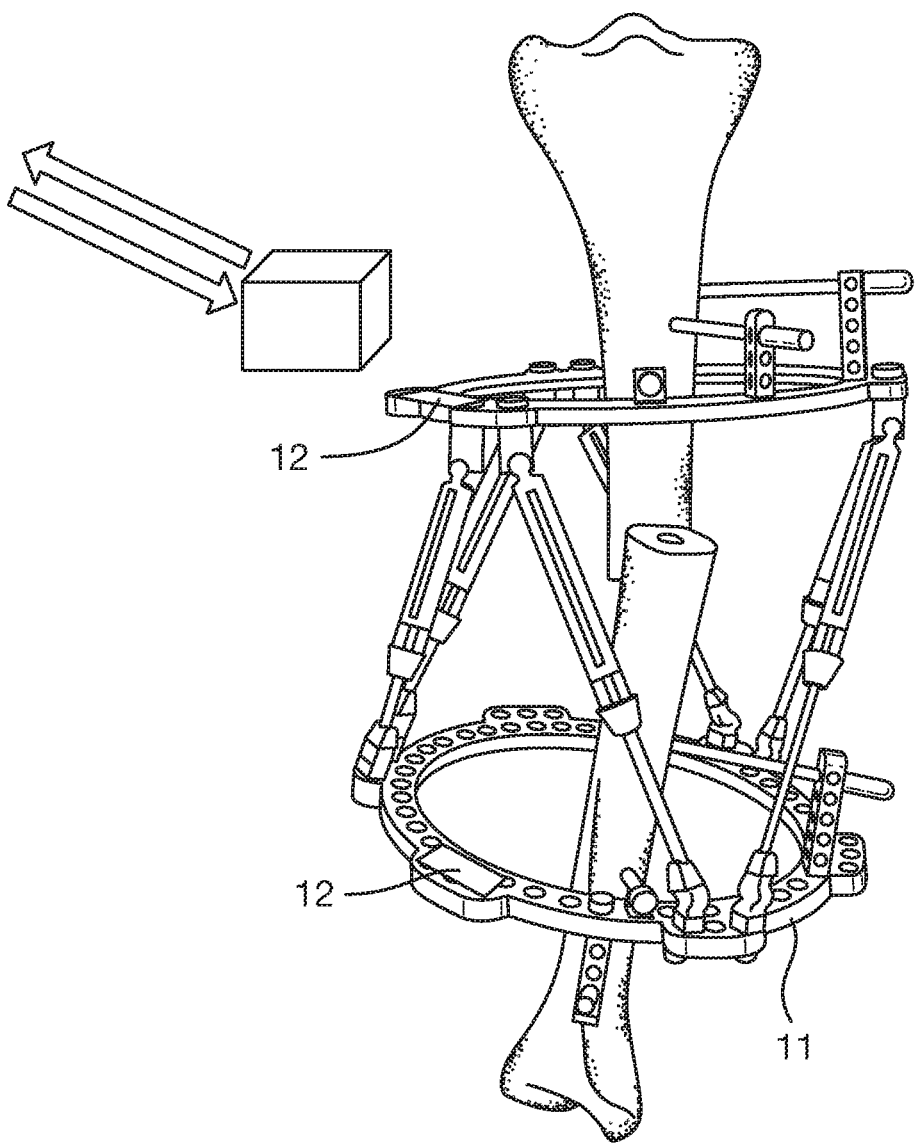
FIG. 5 shows an embodiment of a bone fixation system for ring fixation systems (frames) used for manipulation of the frame configuration.

FIG. 5 illustrates how the system could be used to provide feedback to a bone fixation system, in this case a 'ring-fixation' system (11), in order to provide manipulation commands. Ring fixators are commonly used to provide an aid to reconstruction. If the relative positions of a number of rings are data-logged via one or more suitable sensors (12) and the structure of the ring-system (or frame) is known then the server (4) is able to provide commands for the manipulation of the frame in order to provide the planned alignment of the rings. This could be instructions to the patient who can manipulate the components manually; equally it could be commands to active components that would manipulate the components automatically. The active components could automatically manipulate the components at pre-determined time intervals dependent on how long the bone fixator has been applied for and/or in response to data collected by the bone fixation system. Manipulations to aid healing include stiffening and adjusting the alignment for example. Further to this, the bone fixation system could be used in reconstruction devices to control fixation parameters, to lengthen, align or perform bone transport for example.

Figure 6:
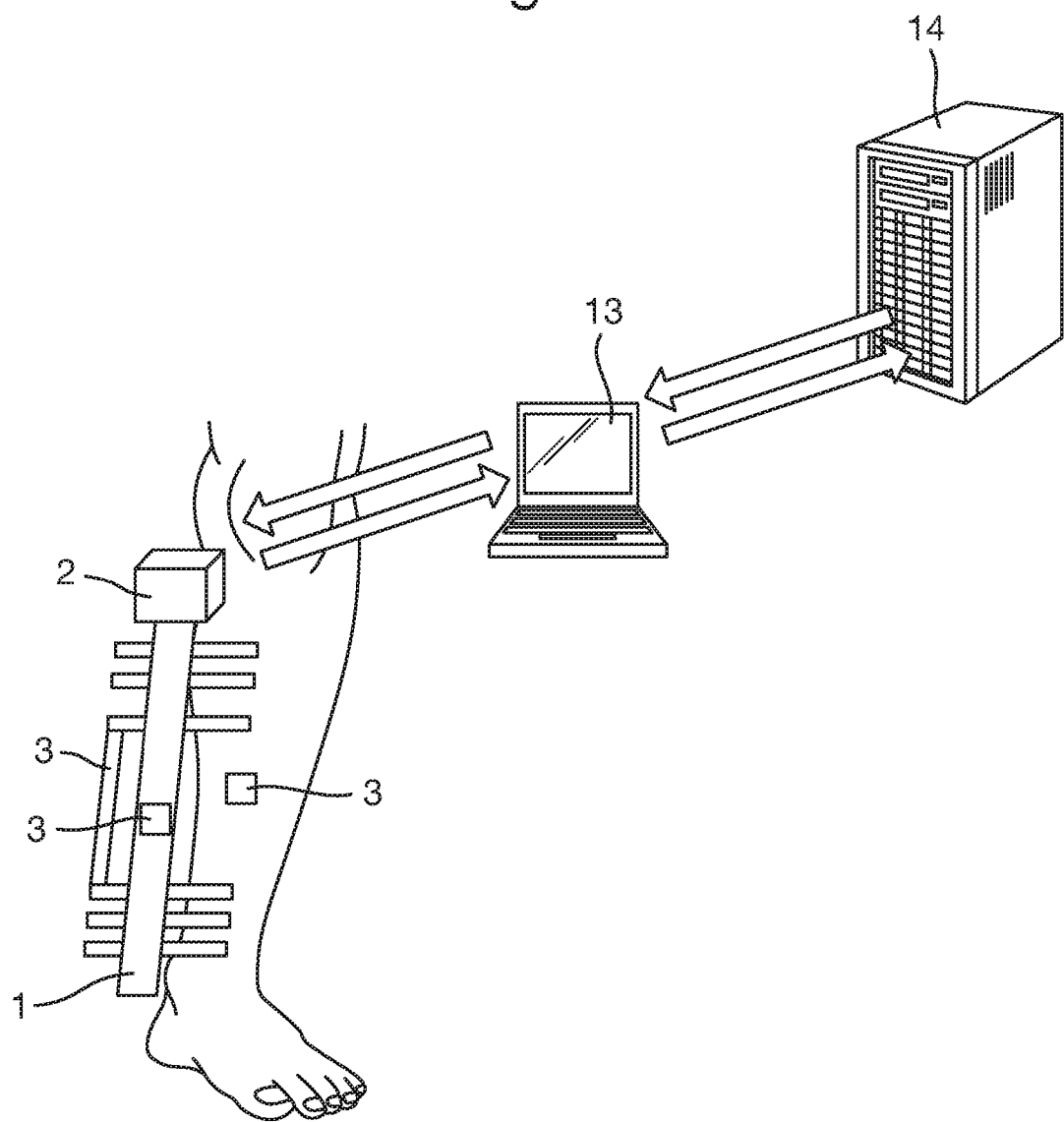
FIG. 6 shows the embodiment of FIG. 1 in communication with a local server.

FIG. 6 illustrates an embodiment of a system using local servers (13). In this embodiment the data-logging system would communicate with a local server (for example the healthcare provider's or the patient's desktop computer), this local server would store and analyse the data but would receive regular updates from the main server (14). Operating much like a standard virus-detection system, local detection and analysis is conducted on the standalone system using a database of information (12). The database of information is updated, regularly, from a main server (14). In turn that main server is updated from the information stored on the standalone system and thus analyses the data on a global scale.

FIG. 7 illustrates the registration of a new data logging system. To ensure patient confidentiality it is envisaged that each data logging unit should have a unique serial number (15); and it is this serial number that is used for all communication and storage of data (16). The only people to know this serial number would be the patient and the healthcare provider. However, as data security increases it could be envisaged that the 'patient ID' could well include pertinent personal details. Registration of the data-logger should incorporate pertinent patient data (17), for example: age, sex, body weight, fracture classification, smoker/non-smoker, alcohol consumption. This data is important for the data analysis that is to follow.

Figure 8A:
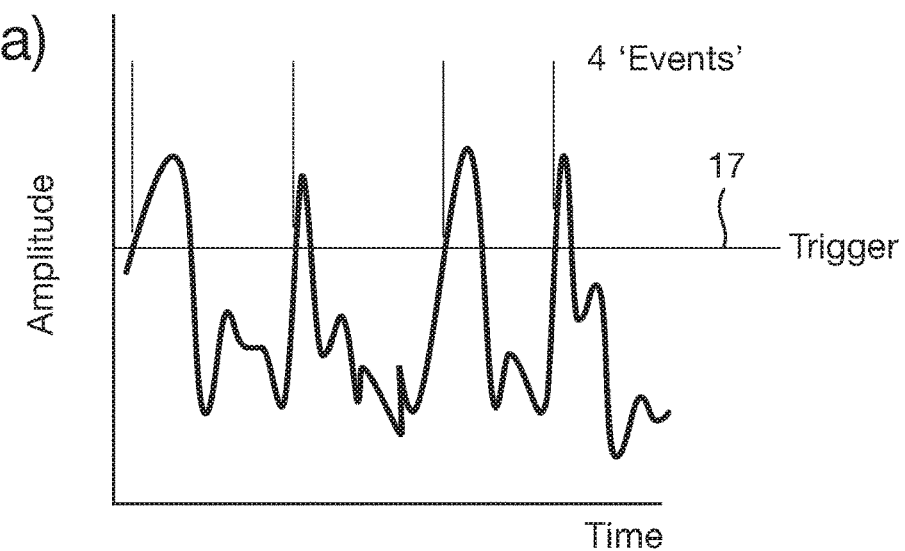
FIG. 8 shows a typical profile for analysis.
Figure 8B:
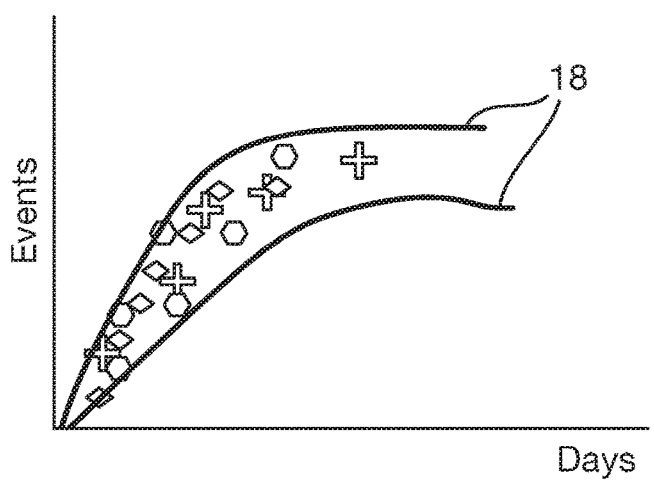
Figure 8C:
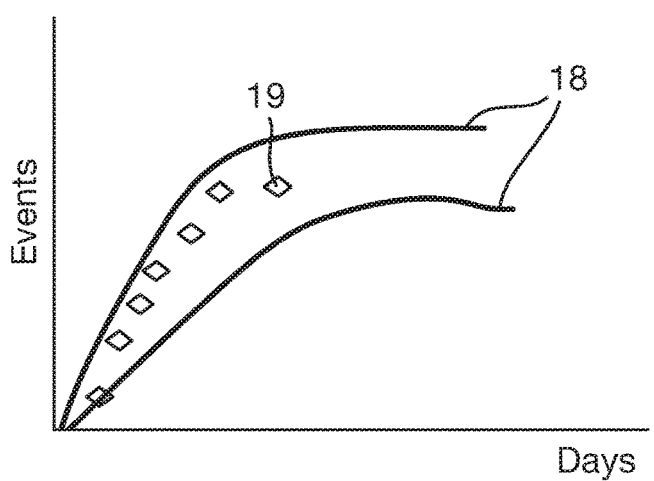

FIG. 8 illustrates how a typical 'profile' may be established. In this instance movement of the fracture is analysed. Whilst the data could come in time domain form (FIG. 8*a*) in this case the data has been analysed to count the number of events per day (frequency domain) by counting how many times a trigger level (17) was exceeded. This data in itself may be useful, but a further plot of events/day versus time (FIG. 8*b*) could be drawn. Once again this data may be useful in itself, but having the ability to compare it against norms is of greater value. Upper and lower quartile graphs (18) would be derived from the analysis of global data discussed previously and could be presented as data-sets based on age, sex smoker etc. The benefits of the global approach of data analysis is that these 'normal' curves could be updatable on a regular basis; this is far more powerful than having a single algorithm fixed in time. Hence FIG. 8*c* illustrates how the data could be presented. An individual patient's 'curve' (19) could then be compared with these norms. Any variance from the norm could be an indicator of a non-compliance, a complication, or a failure (described more fully later). It is easy to envisage that this is not restricted to fracture movement, nor is it restricted to frequency domain data. This power of the data lies in the ability to compare any of the variety of measured parameters for individuals, or groups of individuals, against constantly updated norms.

Figure 9:
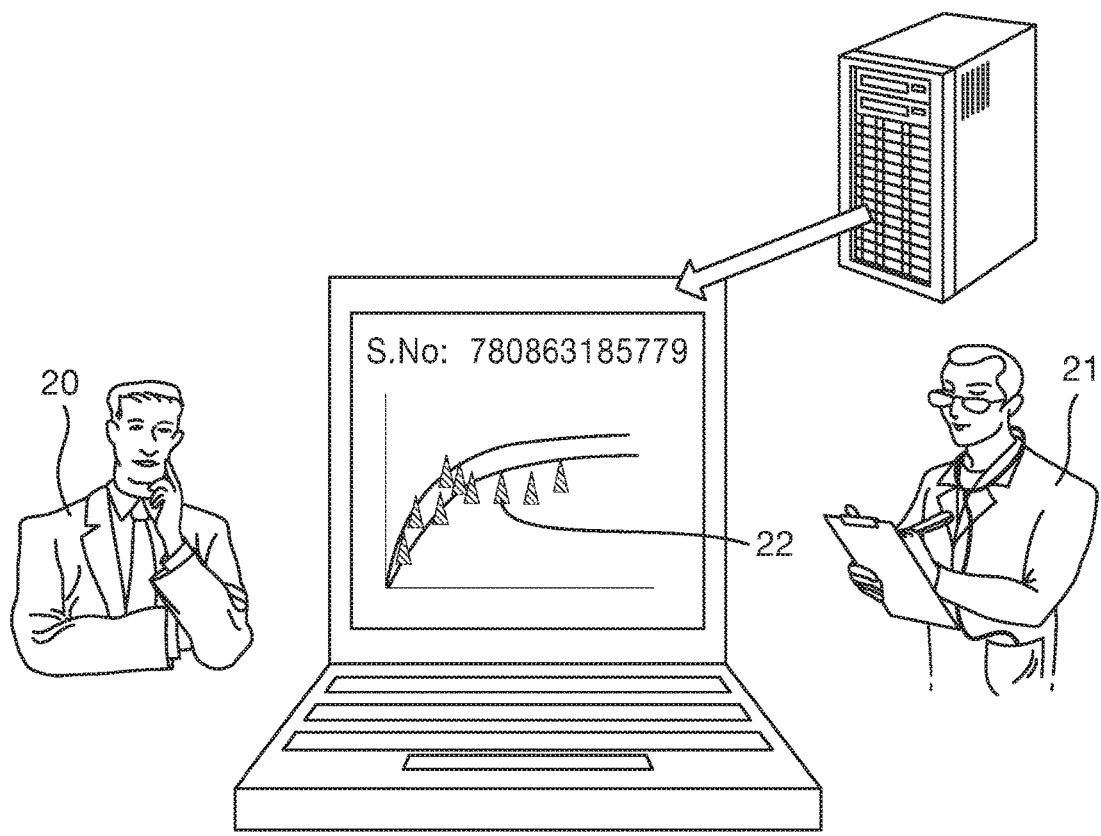
FIG. 9 shows 'pull mode' of data inspection for patient and healthcare provider.

FIG. 9 illustrates how the patient and the healthcare provider would see this data. In this situation the data would be in 'pull' mode. The patient (20), for example, would log onto the system using their unique serial number described earlier. They could then examine their own 'profile' versus norms. They would not be able to see any other individual profile, and no one but their healthcare provider could see theirs. The healthcare (21) provider would also log onto the system but could examine any of the patients' data in their care, either individually or as a group. In this way they could see the progress of an individual patient but also how their own patients, as a whole, compare with the norms.

FIG. 9 also illustrates how the data presented in FIG. 8 could be used as a motivational tool for the patient. For example, the data presented (22) could be number of pedometer events per day versus number of fracture movement events per day. A sedentary patient would not have many pedometer events hence the levels will remain low whereas the upper and lower quartile norms should increase with time to a constant plateau. A patient seeing this data could be motivated to be less sedentary. Equally the same data could be viewed by the clinician as a potential issue related to pain and may wish to discuss this with the patient; but not on an ad hoc basis. There is potential to include an alarm in the data-logger to alert the patient to inactivity that only stops once acceptable activity levels have been achieved. The data-logger may be programmable with pre-determined thresholds such that the alarm is activated when such a threshold is exceeded or not reached. The alarm may be an audio alarm, a visual alarm or both.

Analysis of the data and comparison with norms will enable the system to predict when a fracture is healed; it will also detect the point when the fracture is healed. The system could then warn the healthcare provider to contact the patient, equally it could inform the patient to contact the healthcare provider. With greater confidence in the system it is possible for the system to inform the patient and who would then use the equivalent of a district nurse to remove their fixation.

Figure 10:
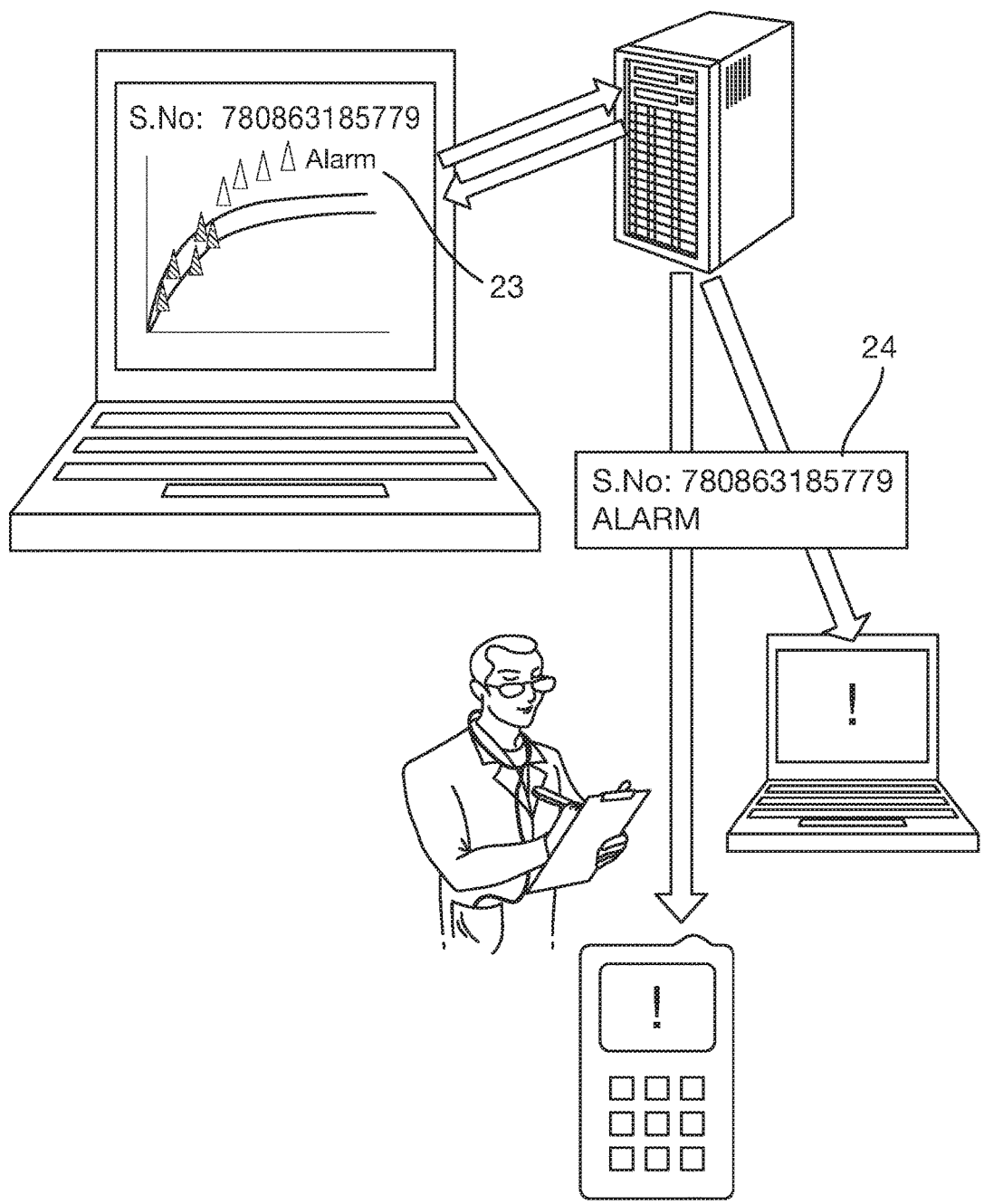
FIG. 10 shows how the system may be used to provide early indication of a potential complication.

One of the hidden benefits is the early detection of complications. FIG. 10, for example, early detection of compartment syndrome could be accommodated using lactic acid and compartment pressure sensors. Detection could lead to a direct alarm to the healthcare provider. Other examples are the early detection of hypertrophic non-union, atrophic non-union, infection, and fixation failure. In this case the server would communicate an alarm (23) to the healthcare provider. Although this could be an immediate alarm time-zones makes this impractical and unnecessary. It is more practical for the healthcare provider to receive an email, text-message (or other electronic data form) from the server (24) at the start of the working day—in their time zone. If the alarm is urgent this could be in the form of a text message to the clinician directly.

Figure 11:
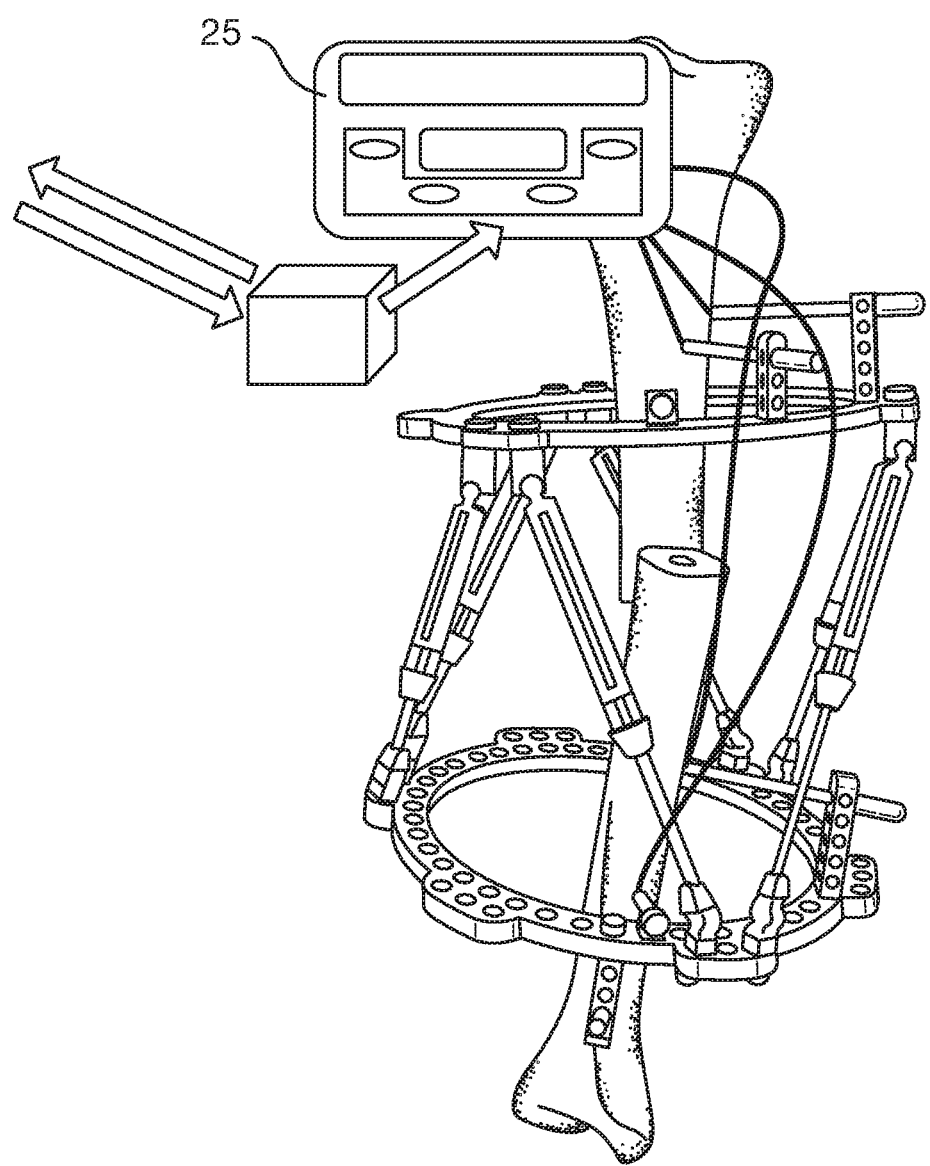
FIG. 11 shows how the system may be used to provide automatic medicinal intervention.

FIG. 11 illustrates a system that incorporates a medical intervention. In this example an ambulatory infusion pump (25) is activated when an infection is detected and suitable medication is administered. A similar system could also inject stimulants in the case of a non-union. It could also start stimulation using electrical, electromagnetic, mechanical, thermal or any other appropriate system.

In an embodiment of the present invention, the bone fixator is a hollow, or cannulated, fixator pin. In this embodiment, a pin may contain one or more transducers, in the form of sensors or otherwise, and these could detect physical, physiological or biological parameters within the bone or limb. Sensors that measure temperature, pressure, oxygen level or tension may be used for example. The cannulated pin may contain means for dispensing or injecting medication, and/or antibiotics, locally to the fracture site. Injection/dispense of the medication and/or antibiotics may be automated. Commands may be sent to active components in the means for dispensing/injecting, providing automated release of the medication/antibiotics.

Figure 12:
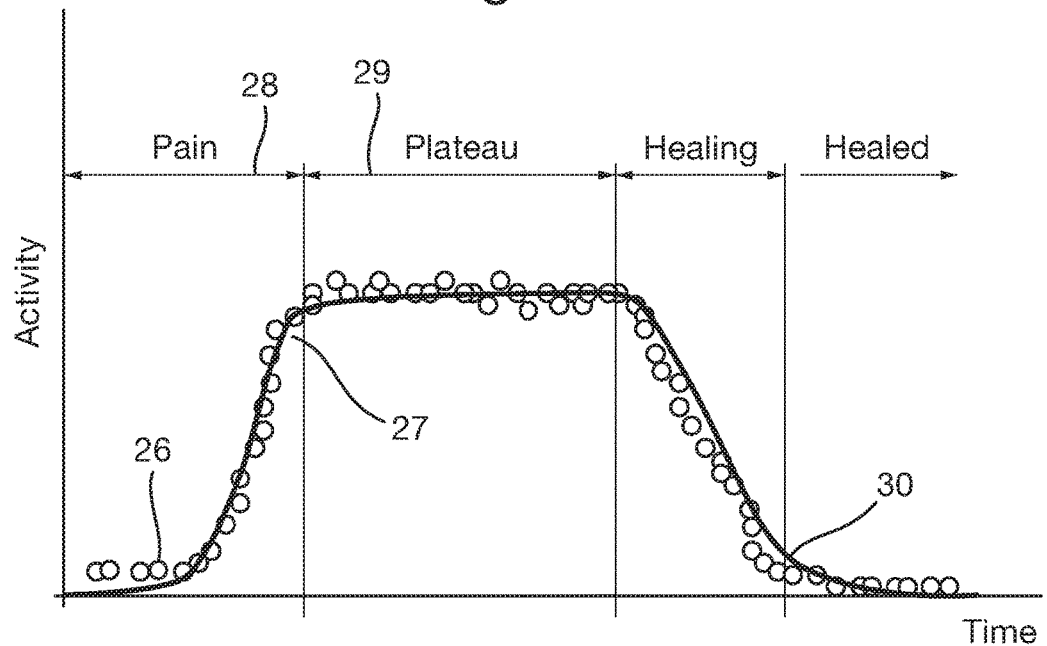
FIG. 12 shows an example of a standard profile for a graph of fracture movement versus time.

FIG. 12 illustrates an example of a standard graph to be used to assess fracture healing. In this case it is a graph of fracture movement events versus time. The number of events per day have been plotted as individual points (26). The standard curve (27) illustrates 4 phases. In phase 1 (28) the fracture is painful hence fracture movement is minimal. As pain subsides and confidence grows the number of events increase until a plateau of normal activity is achieved (29). As the fracture begins to heal events decrease (30) whilst ambulation is maintained. Eventually all fracture movement ceases and the fracture may be considered healed (30); in the case of the tibia this should be no later than 24 weeks or a delayed union may be indicated.

Figure 13:
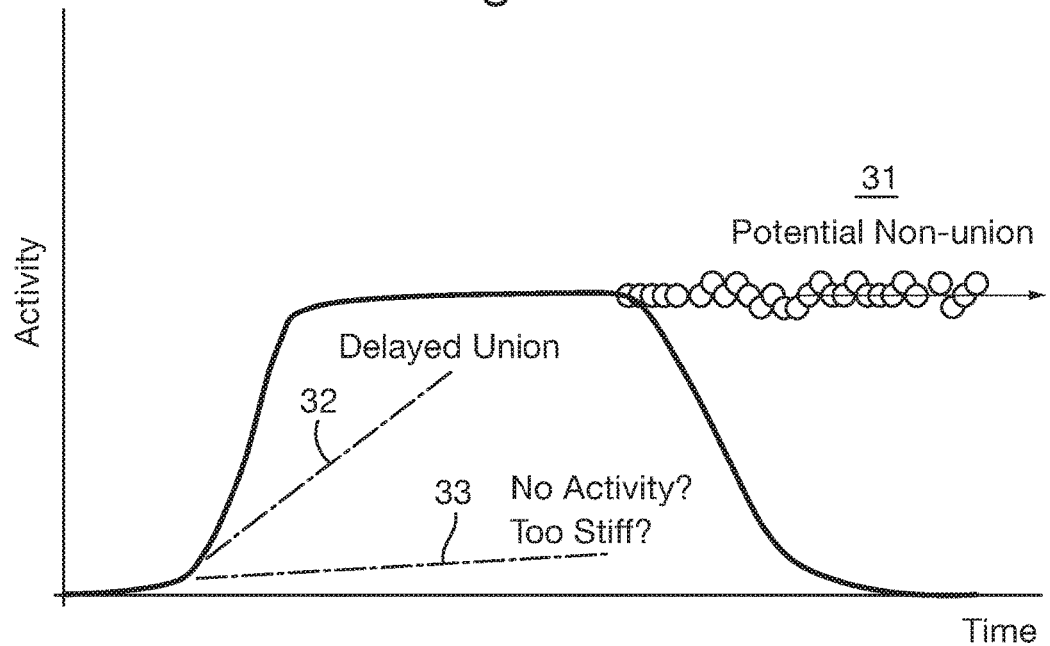
FIG. 13 shows an example of three potential complications that could be detected using the graph in FIG. 12.

FIG. 13 is the graph as illustrated by FIG. 12 but in this case three different scenarios are presented. If the data reaches the plateau but does the movement does not subside (31) then the fracture could be progressing to a non-union, early intervention is essential. Another scenario is that at the start of the pain phase the slope of the graph is abnormally low (32), this could be indicating a delayed union. An extension of 32 is a slope close to zero (33); in this case it could be a sedentary patient or a fixation that is too stiff. In both cases early intervention is highly beneficial.

Figure 14:
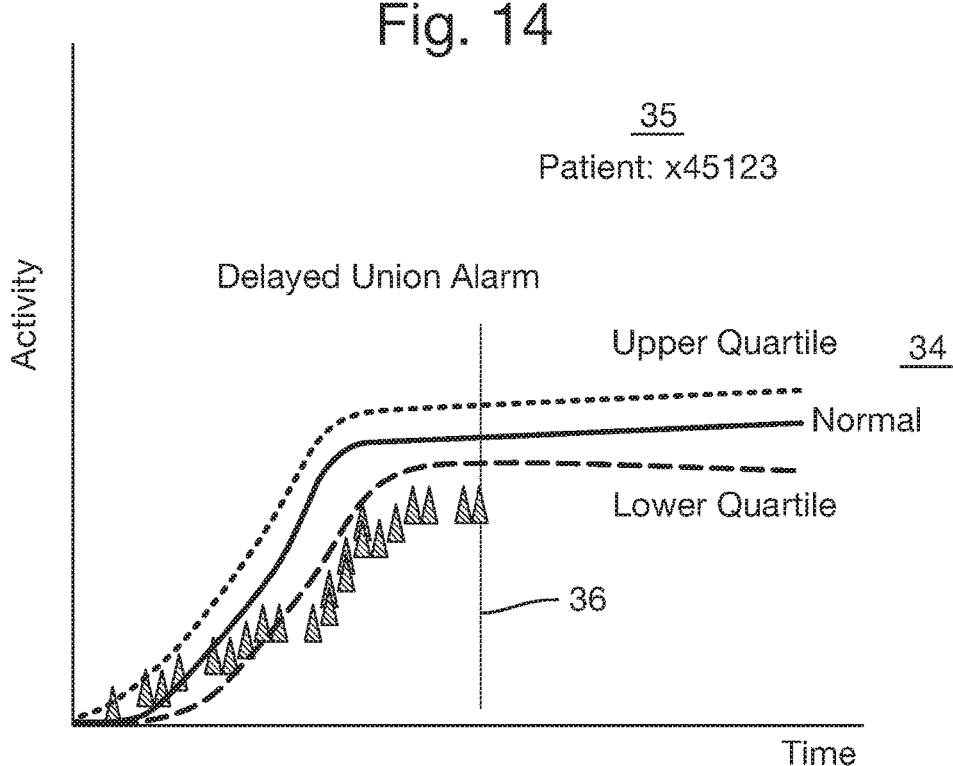
FIG. 14 shows another data set indicating potential complications using normal, and upper and lower quartile data curves.

FIG. 14 is an extension of FIG. 12; in this case the standard graph is illustrated using normal, and upper and lower quartiles (34) as presented in FIGS. 8 and 9. This individual patient's (35) data is falling below the lower quartile and may be indicating a delayed union (36).

Figure 15:
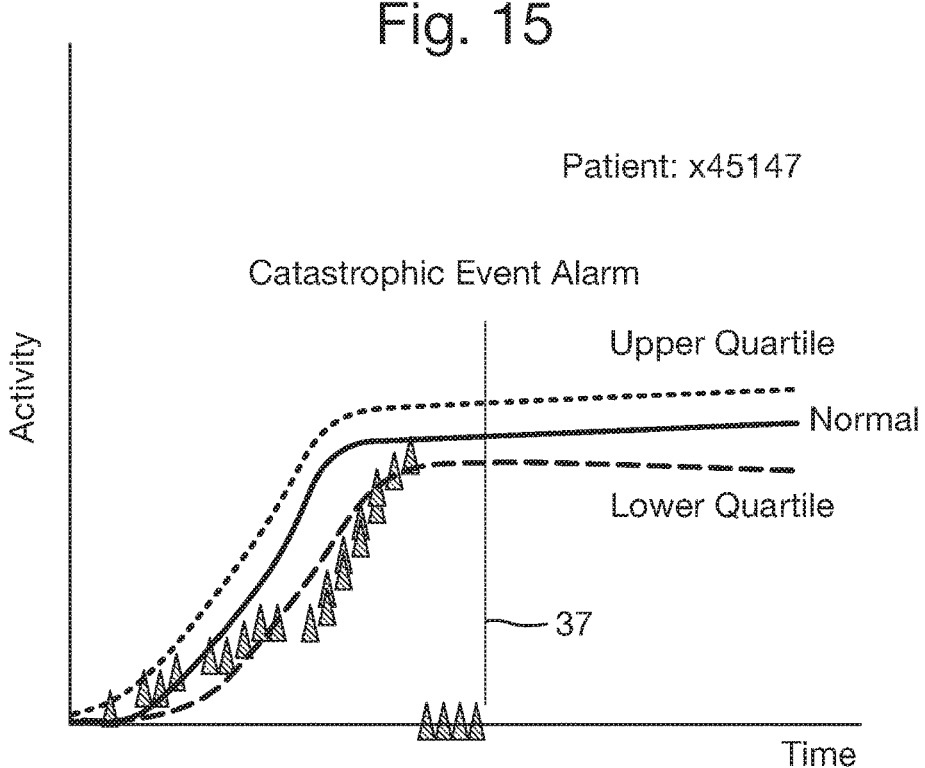
FIG. 15 shows the detection of a catastrophic event.
Figure 16:
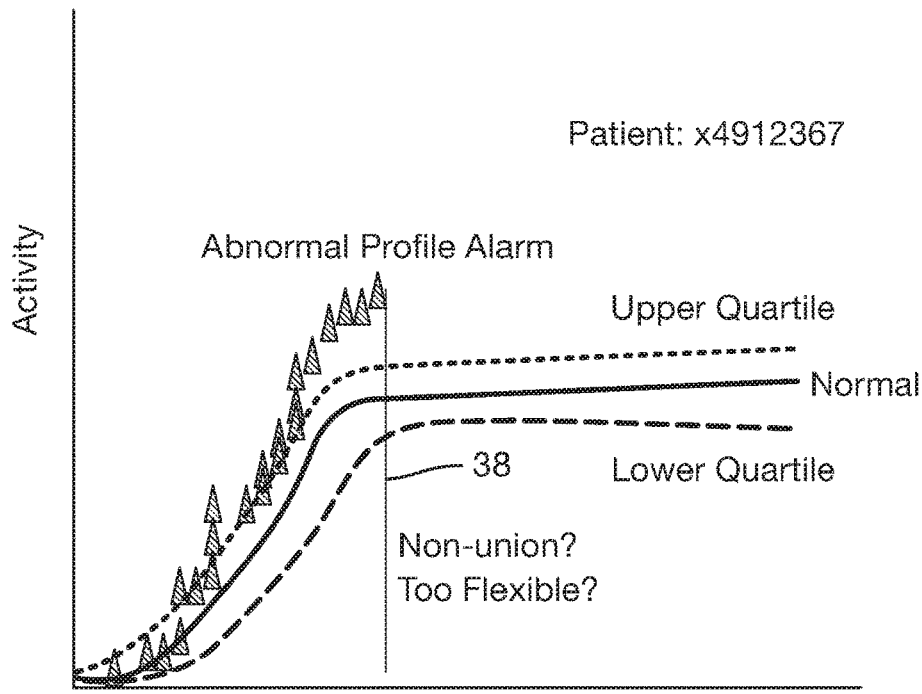
FIG. 16 shows the use of the upper lower quartile data curves detecting further potential complications.

FIG. 15 illustrates another scenario. In this case the patient activity suddenly stops (37). This is a catastrophic failure alarm and could be due to onset of severe pain, it could be the patient has had an accident or is severely ill, or the fixation has catastrophically failed or seized. Early intervention is required. FIG. 16 is the opposite and is indicating too much movement (38); this could be indicating that the fixation is too flexible (which in turn could lead to a mal-union) or it could be that the fracture is progressing to a non-union.

Figure 17:
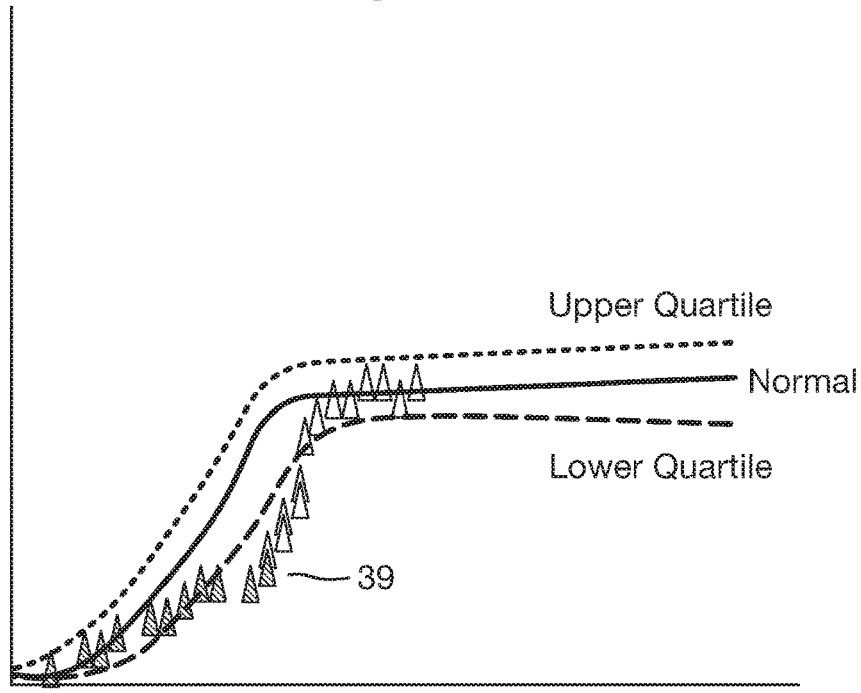
FIG. 17 shows another data set where a patient has been motivated by the data.

FIG. 17 illustrates how the data can provide motivation. In this case the patient has noticed that their activity levels are low (39) and decide to become more mobile. As a consequence their activity returns to within the normal boundaries and their healing pattern is normal.

Figure 18A:
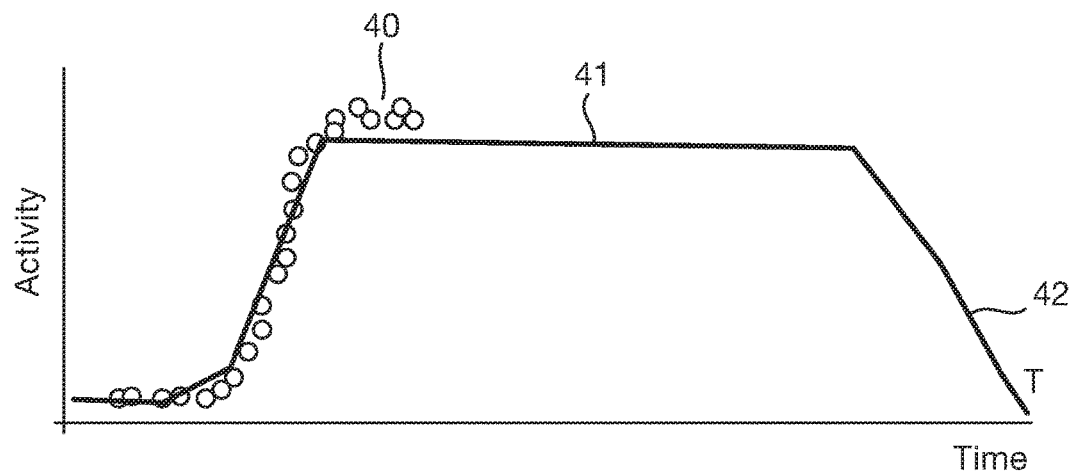
FIG. 18 shows the use of data-fit equations to predict a healing end point.
Figure 18B:
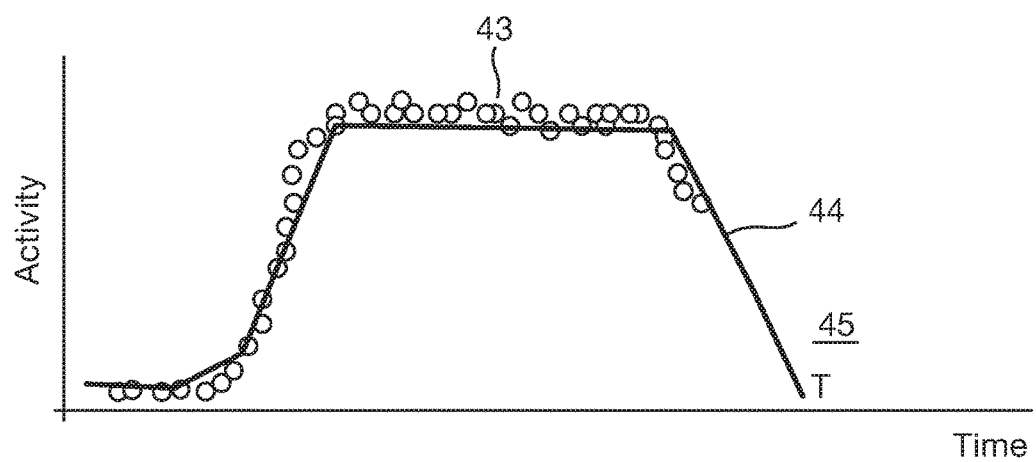

FIG. 18 illustrates how data-fitting can be used to predict healing end-point. As normal data gets collected a known equation can be fitted to predict the overall profile. In FIG. 18(a) the data has only just started (40) and hence a first data-fit (41) obtains a rough estimate of healing end-point, T (42). As more data is collected (43), as in FIG. 18(b), the fitted data produces a curve (44) which will settle to a more consistent estimate for healing end-point, T (45). This information not only informs the healthcare team of the potential appointment for fixation removal but can also motivate patients.

The bone fixation system may comprise a plurality of sensors, which may measure a plurality of parameters. This may be useful in detecting the rate of healing and/or the onset of any particular problems which may be associated with the bone fixation system.

Sensors may include a strain gauge, which may enable the measurement of strain on the bone fixation to be used to assess fracture site excursions. In one embodiment, the fixator body comprises a composite material re-inforced with glass fibres and these fibres may be used as optical strain gauges. Sensors that measure a combination of linear and torsional strains may be used, which may enable measurement of motion in all degrees of freedom at the fracture site. This may be helpful in providing an accurate measure of patient activity level and/or movement at the fracture site.

Combinations of other measurements may be used to assess the rate of healing and/or any problems associated with the bone fixation system. A pedometer, associated with the bone fixation system, may be used to measure the activity of the patient. Activity of the wearer may be helpful in providing a more accurate and reliable measure of bone fracture condition and/or a measure of the progression of healing of the bone fracture. Any temperature monitoring means, associated with the bone fixation system, may be used to measure temperature at the fracture site. Parameters may have thresholds associated with them that enable a reading to be classed as 'high' or 'low', which may depend on the length of time for which the bone fixation system has been applied and/or on how long it has been since the fracture occurred. A processing means may compare the measured data to these thresholds.

Measurement of patient activity, when combined with measurement of the fracture activity, may be beneficial as it may be used to assess the progression of the healing, onset of non-union and/or any subsequent failure of the fixation system. For example, if the patient activity is measured to be high, the fracture activity is measured to be low, and the number of weeks for which the bone fixation system has been applied is less than 7, this may suggest over-stiff fixation has been applied. Alternatively, if the patient activity is measured to be low, the fracture activity is measured to be high, and the number of weeks for which the bone fixation system has been applied is less than 7, this may suggest an unstable fixation or that the fixation is too flexible. Alternatively, if the patient activity is high, the fracture activity is high and the fracture activity is not decaying, this may indicate an atrophic non-union.

In another example, if the patient activity is low, the fracture activity is high and the fracture site temperature is high, this may suggest hypertrophic non-union.

Acceleration of the bone fixation system may also be measured, by way of a one-axis accelerometer connected to the bone fixation system, or otherwise. This may be used to assess whether the bone fixation system, and/or bone or part connected thereto is in a raised position. Measurement of acceleration may be used to assess fracture stiffness; this may be performed by multiplying the acceleration by a bodyweight factor, measuring the bend in the bone fixator and combining these results.

In an embodiment of the present invention, the fixator pin is electrically insulated. This may enable measurement of the potential difference across the fracture site, which may provide indications of the progression of healing.

In any embodiment of the invention, an indicating means, such as an alarm, may additionally be associated with the bone fixation system and may be used to indicate a problem to the user if the measured data is not as expected, if it exceeds or does not reach a threshold for example.

The above embodiments are described by way of example only. Many variations are possible without departing from the scope of the invention as defined in the appended claims.

The invention claimed is:

1. A bone fixation system comprising:
 a bone fixator for application to a bone fracture site;
 a first sensor for measuring a first parameter indicative of load on a bone fracture and generating associated first parameter data;
 a second sensor for measuring a second parameter indicative of an activity level of an individual and generating associated second parameter data;
 a processing means for correlating said first parameter data with said second parameter data to determine a measure of bone fracture condition, and for determining a change in said correlation over time to determine a measure of the change in bone fracture condition over time.

2. The bone fixation system as recited in claim 1 wherein the processing means compares at least said first parameter to a threshold and records an event when this threshold is exceeded.

3. The bone fixation system as recited in claim 2 the system further comprising an indicating means operable to automatically activate when an event is recorded.

4. The bone fixation system as recited in claim 1 wherein the system further comprises an output means for providing an output on at least one of said determinations.

* * * * *